(12) United States Patent
Kaplan (10) Patent No.: US 6,280,961 B1
(45) Date of Patent: Aug. 28, 2001

(54) USE OF TYRAMIDE COATING AND PHYSICAL SEPARATION FOR ISOLATING CELLS OR PARTICLES OF INTEREST

(75) Inventor: David R. Kaplan, Shaker Heights, OH (US)

(73) Assignee: Verve, Ltd., Pepper Pike, OH (US)

( * ) Notice: Subject to any disclaimer, the term of this patent is extended or adjusted under 35 U.S.C. 154(b) by 0 days.

(21) Appl. No.: 09/318,346

(22) Filed: May 25, 1999

(51) Int. Cl.$^7$ ............... G01N 33/53; G01N 33/567; G01N 33/566; C12Q 1/24

(52) U.S. Cl. ............... 435/7.2; 435/7.1; 435/7.2; 435/7.21; 435/7.8; 435/30; 436/501

(58) Field of Search ............... 435/4, 5, 7.2, 7.21, 435/7.24, 7.1, 7.72, 7.9, 30, 7.8, 325, 308.1; 436/63, 537, 546, 805, 813, 501

(56) References Cited

U.S. PATENT DOCUMENTS

| | | | |
|---|---|---|---|
| 5,196,306 | 3/1993 | Bobrow et al. | 435/7.9 |
| 5,583,001 | 12/1996 | Bobrow et al. | 435/7.5 |
| 5,731,158 | 3/1998 | Bobrow et al. | 435/7.5 |

FOREIGN PATENT DOCUMENTS

98/01757  1/1998  (WO).

OTHER PUBLICATIONS

Schönhuber et al. 1997. Improved sensitivity of whole–cell hybridization by the combination of horseradish peroxidase–labeled oligonucleotides and tyramide signal amplification. Applied and Environmental Microbiology. vol. 63. No. 8, pp. 3268–3273.*

Mayer et al. 1997. Biotin–tyramide: a novel approach for electron microscopic immunocytochemistry. Journal of Histochemistry and Cytochemistry. vol. 45(11):1449–1454.*

Melamed et al. 1990. Flow Cytometry and Sorting. Second Edition. John Wiley and Sons, Inc., publication. pp. 374–375.*

Earnshaw et al., "Signal amplification in flow cytometry using biotin tyramine," Cytometry 35:176–179 (1999).

Assenmacher et al., "Commitment of individual Th1–Like lymphocytes to expression of INF–γ Versus IL–4 and IL–10: Selective Induction of IL–10 by Sequential Stimulation of Naive Th Cells with IL–12 and IL–4$^1$," Journal of Immunology 161;2825–2832 (1998).

Bobrow et al., "Catalyzed reporter deposition, a novel method of signal amplification: II. Application to membrane immunoassays," Journal of Immunological Methods 137:103–112 (1991).

Bobrow et al., "Catalyzed reporter deposition, a novel methos of signal amplification: Application to Immunoassays," Journal of Immunological Methods 125:279–285 (1989).

Chao et al., "Immunofluorescence Signal Amplification by the Enzyme–Catalyzed Deposition of a Fluorescent Reporter Substrate (CARD)," Cytometry 23:48–53 (1996).

Classon et al., "Thymic–Shared Antigen–1 (TSA–1): A Lymphostromal Cell Membrane Ly–6 Superfamily Molecule with a Putative Role in Cellular Adhesion," Developmental Immunology 6:149–156 (1998).

Davis et al., "Assessment of a positive selection technique using an avidin column to isolate human peripheral blood T cells subsets," Journal of Immunological Methods 175:247–257 (1994).

Hopman et al., "Rapid Synthesis of Biotin–, Digoxigenin–, Trinitrophenyl–, and Fluorochrom–labeled Tyramides and Their Application for In Situ Hybridization Using CARD Amplification," The Journal of Histochemistry & Cytochemistry 46(6):771–777 (1998).

Kato et al., "Differential expression of the murine Ly–6A/E antigen homolog of human squamous cell carcinoma antigen E48 during Malignant transformation and tumor progression of squamous cell carcinoma line pam 212," Otolaryngol Head Neck Surg 119:408–11 (1998).

Kishimoto et al. (editor), Leucocyte Typing VI: White Cell Differentiation Antigens Proc. of the 6$^{th}$ Int'l. Workshop and Conf. held in Kobe, Japan Garland Publishing Co. (1997) (Table of Contents).

Koshkin et al., "Novel Convenient Synthesis of LNA[2.2.1] Bicyclo Nucleosides," Tetrahedron Letters 39:4381–4384 (1998).

Luxembourg et al., "Biomagnetic isolation of antigen–specific CD8$^+$ T cells usable in immunotherapy," Nature Biotechnology 16:281–285 (1998).

Malisius et al., "Constant Detection of CD2, CD3, CD4, and CD5 in Fixed and Paraffin–Embedded Tissue Using the Peroxidase–Mediated Deposition of Biotin–Tyramide," Journal of Histochemistry & Cytochemistry 45(12):1665–1672 (1997).

Melamed et al. (editors), Flow Cytometry and Sorting: Second Edition Wiley–Liss, Inc. (1990) (Table of Contents).

Nielsen et al., "In vitro separation and expansion of CD4 lymphocytes from HIV–infected individuals without activation of HIV infection," Journal of Immunological Methods 200:107–112 (1997).

(List continued on next page.)

Primary Examiner—Mary E. Mosher
Assistant Examiner—Shanon Foley
(74) Attorney, Agent, or Firm—Foley & Lardner (57) ABSTRACT

The present invention relates to methods of tyramide coating cells or particles for physical separation, using catalyzed reporter deposition and serial amplification staining. A catalyzed reporter deposition or an analyte dependent enzyme activation system is described for detecting and/or quantitating an analyte of interest on the surface of a cell by physical separation. Also described is a method for serial amplification staining by tyramide coating cells or particles which possess an analyte of interest or a solid phase to which an analyte is bound.

20 Claims, 2 Drawing Sheets

OTHER PUBLICATIONS

Partington et al., "A novel method of cell separation based on dual parameter immunomagnetic cell selection," *Journal of Immunological Methods* 223:195–205 (1999).

Pichert et la., "Selection and immunomagnetic purging of peripheral blood CD34+ cells for autologous transplantation in B–cell non–Hodgkin's lymphomas," *Annals of Oncology* 9:51–54 (1998).

Rowley et al., "Isolation of CD34+cells from blood stem cell component using the baxter Isolex system," *Bone Marrow Transplantation* 21:1253–1262 (1998).

Stanciu et al., "Production of IL–8 and IL–4 by positively and negatively selected $CD4^+$ and $CD8^+$ human T cells following a four–step cell separation method including magnetic cell sorting (MACS)," *Journal of Immunological Methods* 189:107–115 (1996).

Sun et al., "Large scale and clinical grade purification of syndecan–1 + malignant plasma cells," *Journal of Immunological Methods* 205:73–79 (1997).

Wysocki et al., "'Panning' for lymphocytes: A method for cell selection," *Proc. Natl. Acad. Sci. USA* 75(6):2844–2848 (1978).

* cited by examiner

//USE OF TYRAMIDE COATING AND PHYSICAL SEPARATION FOR ISOLATING CELLS OR PARTICLES OF INTEREST

INTRODUCTION

The present invention relates to methods of using tyramide coated cells or particles for physical separation, preferably using magnetic separation, cellular panning, column separation and/or fluorescence activated cell sorting (FACS).

BACKGROUND OF THE INVENTION

The following information is presented solely to assist the understanding of the reader, and none of the information is admitted to describe or constitute prior art to the claims of the present invention.

Physical separation of cells or particles may be achieved using a variety of methods, including magnetic separation, cellular panning, column separation, and FACS. The use of magnetic separation is described in Stanciu et al., *Journal of Immunological Methods*, 189:107–115, 1996; Luxembourg et al., *Nature Biotechnology*, 16:281–285, 1998; Sun et al., *Journal of Immunological Methods*, 205:73–79, 1997; Partington et al., *Journal of Immunological Methods*, 223:195–205, 1999; Nielson et al., *Journal of Immunological Methods*, 200:107–112, 1997; and Assenmacher et al., *The Journal of Immunology*, 161:2825–2832, 1998. The use of cellular panning is described Wysocki and Sato, *P.N.A.S.*, 75(6):2844–2848, 1978. Use of column separation is described in Davis et al., *Journal of Immunological Methods*, 175:247–257, 1994. FACS described in Melamed, Lindmo, and Mendelsohn *Flow Cytometry and Sorting* Wiley-Liss, New York, 1990.

Various methods have been described for assaying biological samples with amplified reporter systems. Bobrow et al., U.S. Pat. Nos. 5,196,306, 5,583,001 and 5,731,158, which are all herein incorporated by reference in their totality including any drawings, describe methods for detecting or quantitating analytes using an analyte dependent enzyme activation system as well as catalyzed reporter deposition methods. Specifically, Bobrow et al. describe colorimetric and fluorometric solid phase enzyme immunoassays which are enhanced by amplification of the reporter molecules.

Chao et al., "Immunofluorescence Signal Amplification By The Enzyme-Catalyzed Deposition Of A Fluorescent Reporter Substrate (CARD)", *Cytometry* 23:48–53 (1996), describe a CARD system that uses horseradish peroxidase substrate Cy3.29-tyramide to deposit fluorogen molecules onto fixed tissues and cells or particles as well as proteins bound to nitrocellulose membranes, with up to a 15 fold increase over standard indirect immunofluorescence methods.

Malisius et al., "Constant Detection of CD2, CD3, CD4, And CD5 In Fixed and Paraffin-Embedded Tissue Using The Peroxidase-Mediated Deposition Of Biotin-Tyramide", *The Journal of Histochemistry and Cytochemistry*, Vol. 45(12):1665–1672, (1997), describe a method for enhancing detection of leukocyte antigens in formalin-fixed tissue samples.

SUMMARY OF THE INVENTION

This invention features methods for enhancing the detection and/or quantitation of an analyte of interest on one or more cells or particles, preferably live cells. The invention provides a method for tyramide coating cells or particles for physical separation, wherein cells or particles are preferably exposed to a catalyzed reporter deposition system which results in specific tyramide coating of cells or particles which contain or express an analyte of interest. The invention, however, features physical separation and detection of tyramide coated cells or particles regardless of how the cell or particle is coated with tyramide and encompasses the use of any such cells or particles which can be prepared using various techniques known by those skilled in the art. Thus, the present invention allows for increased detection of an analyte of interest in a sample of cells or particles by use of physical separation methods. Furthermore, the present invention allows for the isolations of cells or particles that express analytes which are present in low copy number in a cell or particle sample.

The term "low copy number" means that the analyte of interest is present on or in the cell or particle but is not represented in an easily detectable amount. An aspect of the present invention is that rare, hard to detect analytes may be readily detected by the increase in the labeling of the cell or particle caused by the amplification of the labeling molecule. Hence, a low copy number analyte, such as the Fas ligand, would not have to be over-expressed in a cell or particle in order for the cell or particle to be isolated by physical separation. The low copy number is preferably less than 20,000 molecules/cellular or particle surface, more preferably less than 10,000 molecules/cellular or particle surface and most preferably less than 5000 molecules/cellular or particle surface.

In a first aspect, the present invention features a method of physical separation which involves coating cells or particles with tyramide and isolating the cells or particles with a physical separation device.

By "tyramide coating" or "coating cells or particles with tyramide" is meant to relate to any process which results in cell or particle surfaces being coated with tyramide, such as the enzyme dependent deposition of tyramide on the surface of cells or particles containing the analyte of interest. In the presence of oxygen radicals, short lived tyramide radicals are formed which form covalent linkages with aromatic molecules such as certain amino acids (tyrosine and tryptophan for example) found in most proteins. Since cell surfaces (and some particle surfaces) have an abundance of proteins, the tyramide radicals bind to the surface of the cell or particle to which it is in closest proximity. The generation of oxygen radicals, by the catalytic activity of the enzymatic portion of the second binding partner and the appropriate substrate, over a period of time, in the presence of tyramide produces tyramide radicals that coat the surface of the cell. The cells or particles preferably are not fixed before contacting with the binding partner specific for the analyte of interest, and have not been treated with a conventional fixation procedure such as methanol fixation. However, the cells or particles may be fixed by procedures known in the art after contacting with the binding partner which is specific for the analyte of interest.

What is meant by "live cells" is that the cells to be assayed for an analyte of interest are viable when contacted with the binding partner for the analyte of interest. In certain embodiments the cells are viable during physical separation. The cells are preferably viable during and after physical separation to allow for selection and/or sorting of cells which have or do not have the analyte of interest, if desired, and used for therapeutic and/or research methods. It is known by those of skill in the art that the cells may also be manipulated to remain in a certain stage of the cell cycle during analysis. It is also understood that the cells may be fixed for analysis after contact with the binding partner specific for the analyte of interest.

By "viable" is meant that the cells are capable of being grown, cultured, or further propagated at the time at which contact with the binding partner for the analyte of interest occurs. Essentially, viable cells are alive and capable of mitotic or meiotic division and further growth after contact with the binding partner specific for the analyte of interest. In a preferred embodiment of the invention, the cells are capable of being grown, cultured, or further propagated after being analyzed by physical separation.

By "cells" is meant the smallest unit of living structure capable of either aided or un-aided existence, composed of a membrane-enclosed interior which may contain a nucleus or nucleoid, free compact DNA, and/or other organelles such as mitochondria, the golgi apparatus, centrioles, endoplasmic reticulum, vacuoles, microsomes, lysosomes, ribosomes and the like. The cells can be bacterial cells as well as eukaryotic cells such as plant cells, yeast or fungal cells or mammalian cells. In a preferred embodiment, the cells are mammalian cells. Examples of various cells available for physical separation exist throughout the art. Cell types can include but are not limited to basal, epithelial, erythrocytes, platelets, lymphocyte, T-cells, B-cells, natural killer cells, granulocytes, monocytes, mast cells, Jurkat, neurocyte, neuroblast, cytomegalic, dendritic, macrophage, blastomere, endothelial, HeLa, tumor, interstitial, Kupffer, Langerhans', Langhans, littoral, tissue cells such as muscle cells, adipose cells, CHO cells, KFL9, K562, enucleated cells and the like as well as cells readily prepared and sold by immunological and microbiological resources currently.

By "particle" is meant any solid or porous support for the expression of the analyte. The term particle may refer to a cell or non-cell analyte and preferably is about the same size as a cell. Those skilled in the art are familiar with various solid particles that can be detected using the methods of the present invention.

By "aided existence" is meant adding components to the buffer or medium containing the cells which allows the cell to remain viable.

In a preferred embodiment, the present invention features a method for tyramide coating cells or particles for physical separation by contacting the cells or particles with one or more of the following; a first binding partner specific for the analyte of interest, a second binding partner with enzymatic activity and which specifically binds to the first binding partner, a substrate for the enzymatic activity of the second binding partner, and a labeling molecule containing tyramide. The tyramide containing labeling molecule is coated on the cells or particles possessing the analyte of interest as a result of the product of the enzymatic activity of the second binding partner and the substrate reacting with the tyramide. A detectable marker may be added after tyramide coating to facilitate physical separation. The detectable marker can be attached to a binding partner specific for the tyramide containing molecule. In a further embodiment, the tyramide containing molecule is comprised of tyramide attached to a detectable marker and a binding partner specific for the binding partner which is bound to the analyte of interest.

By "detectable marker" is meant any type of label that can be added to the particulate or cellular analyte of interest and detected in the methods of the present invention. Those skilled in the art are familiar with a variety of suitable detectable labels.

The term "binding partner" refers to biochemical or chemical molecules such as polypeptides, glycoproteins, glycolipids, lipids, or nucleic acids which bind to the analyte of interest or to a first binding partner which specifically binds to the analyte of interest. Binding partners may be attached naturally through contacting a molecule that is a receptor for the binding partner. The polypeptides can be conjugated proteins, antibodies and the like. Hence, a binding partner may consist of an antibody bound to a label or an enzyme bound to a binding partner, or an antibody bound to a binding partner. Pairs of binding partners can be but are not limited to, (i) streptavidin and biotin, (ii) an antibody and an epitope, (iii) an antibody and a protein, (iv) a protein and a receptor molecule or receptor protein, (v) a nucleic acid and a nucleic acid, (vi) a nucleic acid and a protein, (vii) a hormone and a hormone receptor, (viii) a cytokine and a cytokine receptor. The nucleic acids can be DNA, RNA, mixed oligonucleotides, peptide nucleic acids (PNA), Locked Nucleic Acids (LNA) as described in Koshkin, et al., Tetrahedron Letters 1998 39:4381–4384, which is incorporated herein by reference in its entirety including any drawings, and the like. In a preferred embodiment the binding partner with specificity to a first binding partner which has bound the cellular analyte of interest, has enzymatic activity. It would be clear to one of skill in the art that various combinations of binding partners which are capable of binding by either covalent or non-covalent means can be used in the invention to tyramide coat cells or particles.

By "contacting" is meant bringing the cells or particles into close proximity with the binding partners in a manner which allows the analytes of interest to interact with and bind to binding partner. "Contacting" preferably refers to bringing the cells or particles into close proximity with the binding partners in a manner which allows previously bound partners to interact with unbound partners and thereby bind. "Contacting" may also refer to bringing the cells or particles into close proximity with an enzyme substrate in a manner which allows any previously bound partners which posses enzymatic activity to interact with the substrate for the enzyme.

By "analyte of interest" is meant a molecule in or on the surface of a cell or particle. The molecule can be a protein, glycoprotein, glycolipid, lipid, a nucleic acid, or a biochemical or chemical molecule as defined above. In preferred embodiments the molecule is a cell surface expressed molecule, such as (but not limited to) cell surface ligands, for example, Fas ligand (which binds CD95) and the ligands for CD1 through CD166, surface antigens CD1 through CD166 as disclosed in "Leukocyte Typing VI: White Cell Differentiation Antigens" Edited by Kishimoto et al., Garland Publishing, Inc. New York 1997, which is incorporated herein by reference in its entirety including any drawings, hormone receptor molecules, cytokine receptor molecules, MHC class I, MHC class II, cell receptors for IgG, and IgE, cell receptors for complement components such as receptors for C3a, C5a, CR1 and CR3, T-Cell or B-Cell receptor molecules, viral antigens, tumor antigens, histocompatibility antigens, differentiation antigens, T-cell antigen, Ly antigen, Ly-6 (Classon et al., Dev. Immunol. Vol. 6(1–2):149–156, 1998, Kato et al., *Otolaryngol Head Neck Surg.* Vol. 119(4):408–411, 1998, IgD, IgM and the like. Also included are cell surface molecules within families of molecules such as those disclosed above.

In another embodiment, the cell is transformed to express a surface molecule that is not a natural component of the cell. These transformed cells or particles may express molecules such as bacterial antigens, viral proteins or cellular proteins normally expressed intra-cellularly and engineered for secretion and expression on the surface of the cell. This type of transformation is common and routinely preformed by those in the art and generally involves the insertion of exogenous DNA or RNA constructs composed of a sequence specific for the molecule of interest wherein the construct is configured and arranged in a manner suitable for expression when inside of the cell. Moreover, only a proportion of cells that have been treated to express a surface molecule that is not a natural component of the cell actually express the molecule; thus, it is often desirable to physically separate cells that express the molecule from cells that do not. In addition the analyte of interest can be a molecule which has been inserted into the cell by experimental methods. This molecule may be a dye or a chemical molecule which the cell can internalize or bind on it's surface.

The term "enzymatic activity" refers to the ability of the binding partner to act as a catalyst to induce chemical changes in other substances. In one embodiment the enzymatic activity catalyzes the dehydrogenation (oxidation) of various substances in the presence of hydrogen peroxide. In a preferred embodiment the enzymatic activity refers to the reaction between the horseradish peroxidase portion of a binding partner and a peroxide substrate. The enzymatic activity could also be the result of the reaction between enzymes such as, but not limited to, oxidases, phosphatases, esterases and glycosidases and their respective substrates.

By "labeling molecule" is meant that substance which ultimately binds to the cell or particle or binding partner attached to the cell or particle that leads to the deposition/coating of tyramide on the surface of the cell. The labeling molecule can be tyramide alone or tyramide conjugated to a binding partner for either the analyte of interest or a first binding partner, or tyramide conjugated with a binding partner. In one embodiment the labeling molecule comprises a phenol group and is capable of being conjugated with a molecule such as biotin or a binding partner. In a preferred embodiment the labeling molecule is tyramide conjugated with biotin. The labeling molecule generally brings tyramide into close proximity with the cell or particle. Once bound to the cell or particle the biotin-tyramide conjugate is available for binding to a detectable marker that allows for cellular isolation such as a streptavidin-fluorochrome conjugate.

By "detectable marker" is meant that substance or molecule which is attached to the binding partner or added to tyramide labeled cells or particles, and which can be detected so that the labeled cells or particles can be isolated by physical separation.

In preferred embodiments of the invention the method for tyramide coating cells or particles results in increased isolation of cells or particles by physical separation.

By "standard physical separation" is meant isolation of a proportion of cells that express a given property such as expression of an analyte among other cells that do not express this property by commercially available devices for physical separation analysis of cell samples or such other devices currently known or which can be produced based on currently available technology. Standard physical separation can encompass magnetic separation, cellular panning, column separation, and/or fluorescence activated cell sorting (FACS). The analysis may involve quantitation and/or detection of the analyte and may involve sorting or harvesting the cells or particles possessing the analyte of interest. Physical separation will be useful when a population of cells or particles are heterogenous in regards to the expression of a given analyte such as a cell surface molecule. Thus, physical separation refers to the isolation of subpopulations within a population of cells or particles based on the expression of the given analyte.

In an additional embodiment of the invention the binding partner which is specific for the analyte of interest is chemically attached to biotin, or biotinylated by methods which are routine and well known in the art. In another embodiment the binding partner is a biotinylated antibody. In a further embodiment the binding partner which is specific for the analyte of interest is a biotinylated construct combining a protein or nucleic acid molecule with biotin. Linking the respective binding partners to the biotin molecule prepares the binding partner to be readily available to binding partners which have been chemically attached to the glycoprotein streptavidin which has high affinity for binding the biotin molecule. Those in the art would readily recognize that other proteins which specifically bind molecules with similar characteristics as biotin and streptavidin and which are readily attached to antibodies or cellular analytes are within the scope of the present invention.

In another embodiment of the invention the binding partner which possesses enzymatic activity is a streptavidin-enzyme conjugate. Streptavidin is a 60,000 Dalton extracellular protein of *Streptomyces avidinii* with four high-affinity biotin binding sites. Analogues of Streptavidin or recombinant proteins of Streptavidin are within the scope of the present invention. Streptavidin is readily conjugated with other proteins and such conjugates can be but are not limited to streptavidin-peroxidase, streptavidin-hydrolase, streptavidin-oxidase, streptavidin-glycosidase and streptavidin-phosphatase. In a preferred embodiment the streptavidin-enzyme conjugate is streptavidin-horseradish peroxidase. The binding partner which possesses enzymatic activity is also called the enzyme in different embodiments of the invention.

An additional embodiment of the present invention features a method for tyramide coating cells or particles for physical separation by contacting the cells or particles with the following; a first binding partner specific for a first analyte of interest, a second binding partner with enzymatic activity and which specifically binds to the first binding partner, a substrate for the enzymatic activity of the second binding partner, and a labeling molecule containing tyramide. After tyramide coating and the addition of a detectable marker, the cells or particles are contacted with a third binding partner specific for a second analyte of interest, a fourth binding partner with enzymatic activity and which specifically binds to the third binding partner, a substrate for the enzymatic activity of the fourth binding partner, and a labeling molecule containing tyramide and specific for the third or fourth binding partners. The tyramide containing labeling molecules are coated on the cells or particles possessing the analytes of interest as a result of the enzymatic activities of the second and fourth binding partners causing tyramide deposition. Detectable markers are added after tyramide coating to facilitate physical separation. In this way, isolation of cells can be based on the expression of more than one analyte.

In another embodiment the present invention provides a method for tyramide coating cells or particles for double label analysis for physical separation by contacting the cells or particles with the following; a first binding partner specific for a first analyte of interest, a second binding partner with enzymatic activity and which specifically binds to the first binding partner, a substrate for the enzymatic activity of the second binding partner, and a labeling molecule containing tyramide. In one embodiment of the present invention, after tyramide coating and the addition of a detectable marker, the cells or particles are contacted with a third binding partner specific for a second analyte of interest. The third binding partner is preferably conjugated to a detectable marker. In a further embodiment, the third binding partner is added with the addition of the first binding partner. In an even further embodiment of the present invention, the third binding partner is added at anytime during double label analysis as this third binding partner, which is preferably conjugated to a detectable marker, is not directly associated with the amplification of tyramide coating associated with the first and second binding partners.

By "double label" is meant labeling the cells or particles by tyramide coating for physical separation and further labeling the cells or particles for a second isolation by standard physical separation methods.

In another embodiment the present invention provides a method for tyramide coating cells or particles for physical separation using serial amplification by contacting the cells or particles with the following; a first binding partner specific for a first analyte of interest, a second binding partner with enzymatic activity and which specifically binds to the first binding partner, a substrate for the enzymatic activity of the second binding partner, and a labeling molecule containing tyramide which is attached to and/or contains a binding partner which enables the conjugated tyramide-binding partner labeling molecule to bind to the second binding partner with enzymatic activity. After this initial tyramide coating, the cells or particles are further contacted with additional second binding partner, additional substrate for said second binding partner, and additional labeling molecule containing tyramide. The sequential addition of both the labeling molecule (i.e. tyramide or another detectably labeled phenol attached to biotin) that can bind to the second binding partner with enzymatic activity and the second binding partner, can be repeated as many times as necessary to achieve the desired level of deposited labeling molecule, detectable label, or signal. This novel procedure results in the amplification of labeling molecules deposited on the cell surface. After the desired number of amplifications or sequential additions, the presence of the labeling molecule containing tyramide is detected by the addition of a detectable marker which binds to the labeling molecule, and, is capable of either directly or indirectly generating a signal. This novel process can be repeated as many times as necessary and results in further tyramide coating of the cells or particles and an enhanced detection of low copy number analytes.

By "serial amplification" is meant contacting the cells or particles or an analyte of interest which is bound to a solid phase with repeated coatings of tyramide by additionally contacting the cells or particles with labeling molecules and enzyme-substrate binding pairs.

Hence, an additional aspect of the present invention provides a method for isolating cells or particles expressing an analyte of interest by tyramide coating using a serial amplification procedure, by contacting the bound analyte with the following; a first binding partner specific for the analyte of interest, a second binding partner with enzymatic activity and which specifically binds to the first binding partner, a substrate for the enzymatic activity of the second binding partner, and a labeling molecule containing tyramide which is attached to and/or contains a binding partner which enables the conjugated tyramide-binding partner labeling molecule to bind to the second binding partner with enzymatic activity. After this initial tyramide coating, the analyte is further contacted with additional second binding partner, additional substrate for said second binding partner, and additional labeling molecule containing tyramide.

The sequential addition of the labeling molecule (i.e. tyramide or another detectably labeled phenol attached to bioting) that can bind to the second binding partner with enzymatic activity and the second binding partner can be repeated as many times as necessary to achieve the desired level of deposited labeling molecule, detectable label, or signal. This novel procedure results in the serial amplification of labeling molecules deposited on the solid phase. After the desired number of serial amplifications or sequential additions, the presence of the labeling molecule containing tyramide is detected by the addition of a detectable marker which binds to the labeling molecule and is capable of either directly or indirectly generating a signal. This novel process can be repeated as many times as necessary and results in further tyramide coating of the solid phase and enhanced detection of low copy number analytes.

By "solid phase" is meant supports as used in assays, which are well known by those of skill in the art, which include (but are not limited to) synthetic polymer supports, such as polystyrene, polypropylene, substituted polystyrene, e.g., laminated or carboxylated polystyrene; polyacrylamides; polyamides; polyvinylchloride, and the like; glass beads; agarose; nitrocellulose; nylon; polyvinylidenedifluoride; surface-modified nylon and the like. Preferably the solid phase is chosen or configured so that it contains an excess of proteins that do not bind to the binding partner which is specific for the analyte of interest.

In another embodiment the present invention provides a diagnostic method for tyramide coating cells or particles for physical separation by removing cells or particles from a patient and contacting the cells or particles with the following, a first binding partner specific for the analyte of interest, a second binding partner with enzymatic activity and which specifically binds to the first binding partner, a substrate for the enzymatic activity of the second binding partner, and a labeling molecule containing tyramide, and a detectable marker.

By "diagnostic method" is meant the determination of the nature of a disease. Preferably the disease is caused by a cell, or a changed cell, such as a cancerous cell or a virally infected cell, or a mutated cell, which has a known cell surface analyte. Examples of such methods include but are not limited to determining the phenotype of a lymphoma or leukemia, determining the immunological status of a patient with AIDS or with a primary immunodeficiency syndrome such as severe combined immunodeficiency disease.

In an additional aspect, the present invention provides a method for selecting cells or particles for therapeutic purposes by tyramide coating cells or particles which possess an analyte of interest, and selecting the cells or particles for therapeutic purposes.

By "therapeutic purposes" is meant the selection of cells from a sample of heterogeneous cells taken from a patient for use in the treatment of abnormal conditions.

As an example, cells selected by using methods of the invention are useful in patients requiring bone morrow transplantation. Bone marrow transplantation has involved two procedures that utilize the selection of cells or particles based on surface analyte composition for diagnostic and purposes. A first example procedure which involves selection of cells positive for the cell surface analyte CD34 using antibodies to identify the cells has been used for reconstitution of bone marrow function after marrow ablative chemo-radiotherapy. See Rowley et al., "Isolation of CD34+ cells from blood stem cell components using the Baxter Isolex system" *Bone Marrow Transplantation* Vol. 21:1253–1262 (1998), which is incorporated herein by reference in its entirety including any drawings.

The use of tyramide coating for isolating CD34 positive cells would be advantageous because the technique results in a greater distinction between positive and negative cells and allows for detection of cells that express lesser amounts of the analyte, thereby enhancing physical isolation. Furthermore, malignant cells have been purged from bone marrow for autologous transplantation. Purging has used many different technologies including antibody mediated identification of the malignant cells. See Pichert et al., "Selection and Immunogenetic Purging of Peripheral Blood CD34 Positive Cells for Autologous Transplantation in B-cell Non-Hodgkin's Lymphomas" Ann. Oncol. Vol. 9:51–54. (1998). For identification of malignant cells in blood or bone marrow using antibodies, the amplification labeling procedure would be advantageous because it would allow for detection of cells that express lesser amounts of the analyte, thereby resulting in a more complete removal of the malignant cells.

By "patient" is meant an organism which is a donor or recipient of explanted cells or the cells themselves. Preferably, a patient is a mammal or mammalian cells. More preferably, a patient is a human or human cells.

In another embodiment, the present invention provides an antibody-binding partner conjugate configured and arranged for use with methods for tyramide coating cells or particles for physical separation.

In additional embodiment, the present invention provides a device for physical separation containing tyramide coated cells or particles.

In another embodiment, the invention is a method of physical separation wherein the improvement involves coating cells or particles with tyramide.

In a further embodiment the present invention provides a kit for use with a method of tyramide coating cells or particles for physical separation. The kit includes materials for tyramide coating cells or particles and/or detecting such cells or particles by physical separation. The kit preferably contains components such as, but not limited to, premade buffers, amplification reagents, and a detailed protocol. The premade buffers of the kit of the invention are physiological mediums of a pH which supports the viability of the cells. In one aspect the premade buffers are FICOLL®HYPAQUE® (an aqueous solution comprising a neutral, branched hydrophilic sucrose polymer having an average molecular weight of 400,000 and sodium diatrizoate) with 0.01% hydrogen peroxide, isotonic buffered saline and 0.005% sodium azide at a pH of between 7.3 and 7.5, and Bovine Serum Albumin at 1%. In further embodiments the kit contains isotonic buffered saline with 0.005% azide at a pH of between 7.3 and 7.5, FICOLL®HYPAQUE® (an aqueous solution comprising a neutral, branched hydrophilic sucrose polymer having an average molecular weight of 400,000 and sodium diatrizoate), streptavidin-horseradish peroxidase, peroxide, biotin-tyramide, streptavidin-iron oxide and detailed protocol.

The amplification reagents include the components of the invention which are responsible for generating tyramide radicals and hence the subsequent coating of the cell which contains or displays the analyte of interest. These amplification reagents can include but are not limited to peroxide, conjugated-peroxidase, tyramide, and conjugated tyramide. In another embodiment of the invention the amplification reagents include a conjugated antibody-enzyme component such as an antibody-horseradish peroxidase conjugate.

In yet another embodiment of the invention the kit contains an analyte specific antibody conjugate in it's own buffer which is to be used in the assay. Such an antibody conjugate can be, but is not limited to, an antibody-biotin conjugate or an antibody-horseradish peroxidase conjugate. The antibody may be specific for, but not limited to, the following cellular analytes, cell surface ligands such as Fas ligand (which binds CD95) and ligands for CD1 through CD166, surface antigens CD1 through CD166 as disclosed in "Leukocyte Typing VI: White Cell Differentiation Antigens" Edited by Kishimoto et al., Garland Publishing, Inc. New York 1997, supra, hormone receptor molecules, cytokine receptor molecules, MHC class I, MHC class II, viral antigens, tumor antigens, cell receptors for IgG, and IgE, cell receptors for complement components such as receptors for C3a, C5a, CR1 and CR3, T-Cell or B-Cell receptor molecules, T-cell antigen, Ly antigen, Ly-6 (Classon et al., Dev. Immunol. Vol. 6(1–2):149–156, 1998, Kato et al., Otolaryngol Head Neck Surg. Vol. 119(4):408–411, 1998, IgD, IgM and the like. Also included are cell surface molecules within families of molecules such as those disclosed above.

In a further aspect, the invention features a device for serial amplification and/or multiparameter analysis of a sample. Preferably such a device is configured and arranged to repeat the addition of a second binding partner with enzymatic activity and a labeling molecule as described above. One of skill in the art would recognize that a device of this manufacture would be configured to incorporate the addition of a sample believed to possess an analyte of interest, the addition of the binding partners of the method, as described above, and would include instrumentation which incorporates intermediate washing steps which are necessary for immunoassays such as physical separation, ELISA, radio-immunoassays, analyte dependent enzyme activation system (ADEAS) assays, catalyzed reporter deposition amplification assays, and the like, or other immunohistochemical staining methods.

Another aspect of the present features a method for detecting or quantitating an analyte in an assay wherein said method comprises using an analyte dependent enzyme activation system, wherein the method is an improvement which comprises repeatedly adding enzyme, substrate and labeling molecule, and wherein repeatedly added labeling molecule is deposited on the cell or a solid phase and can either directly or indirectly generate a signal which can be detected or quantitated.

By "repeatedly added" is meant the enzyme, substrate and labeling molecule are further added after they are initially introduced to the sample. Such an addition can be considered a cycle, where the first addition represents one, or the first, tyramide (detectably labeled phenol) coating event, and subsequent "repeated additions" represent further cycles of tyramide coating. In a preferred embodiment the enzyme, substrate and labeling molecule are repeatedly added more than once. Hence, in a preferred embodiment at least two cycles of tyramide coating are performed.

What is meant by "analyte dependent enzyme activation system" is a labeling method which incorporates a first binding partner specific for an analyte of interest, a second binding partner with enzymatic activity, a substrate for said activity, and a detectably labeled phenol, such as a tyramide-biotin conjugate. The detectably labeled phenol is capable of being activated by the reaction between the enzyme and the substrate in a manner which results in it's being deposited on the surface to which the first binding partner has bound to the analyte of interest. Further examples of analyte dependent enzyme activation systems are discussed in Bobrow et al., U.S. Pat. No. 5,583,001 (1996) and U.S. Pat. No.

5,196,306 (1993), which are herein incorporated by reference in their entirety including any drawings or figures.

The present invention also provides a composition for magnetic separation of cells or particles containing tyramide bound to iron oxide. Also featured is a composition for cellular panning containing tyramide bound to a plate or dish. A composition for column separation of cells or particles is also provided containing tyramide bound to one or more beads. Tyramide can be conjugated to protein that has been derivatized with N-hydroxysuccinimide in the presence of a carbodiimide. The conjugation forms an amide bond so that tyramine becomes a tyramide. Protein conjugates of tyramide, including specifically tyramide-green fluorescent protein, are also featured in the present invention. This conjugate could be used for isolation of cells via FACS. Green fluorescent proteins are a class of proteins with many members that are naturally fluorescent. Proteins that have been conjugated with fluorescent molecules are also featured in the present invention. In another embodiment of the present invention, tyramide-bovine serum albumin is adhered to plastic plates or dishes for panning. Tyramide beads for column separation and tyramide beads containing iron oxide for magnetic separation are also provided by the present invention. Tyramine can be conjugated with either type of beads either directly using the same chemistry or via proteins. For direct conjugation the beads would be carboxylated and the same chemistry for binding proteins would apply. Otherwise, beads with attached proteins could also be used. Those skilled in the art will be aware that other chemistries could be used to attach tyramines to either proteins or beads.

The summary of the invention described above is not limiting and other features and advantages of the invention will be apparent from the following detailed description of the invention and from the claims. One of skill in the art would readily recognize that in certain aspects of the invention additional steps may be added, such as washing steps, which are practiced regularly when performing assays which require addition of multiple binding partners or detectable molecules. Such procedures are described herein in the following examples and have been described in the art. Furthermore, the methods described herein have been disclosed, in some instances, in a sequential manner which one of skill in the art would readily recognize as convenient, but not necessary. Hence, in certain aspects of the invention, the binding partners may be added in a sequential manner, simultaneously or in an arbitrary manner which can still result in the binding of an analyte of interest to a binding partner resulting in the tyramide coating of cells or particles for physical separation or the serial amplification of tyramide coating cell surfaces or solid phases for the detection of an analyte of interest.

Figure 1:
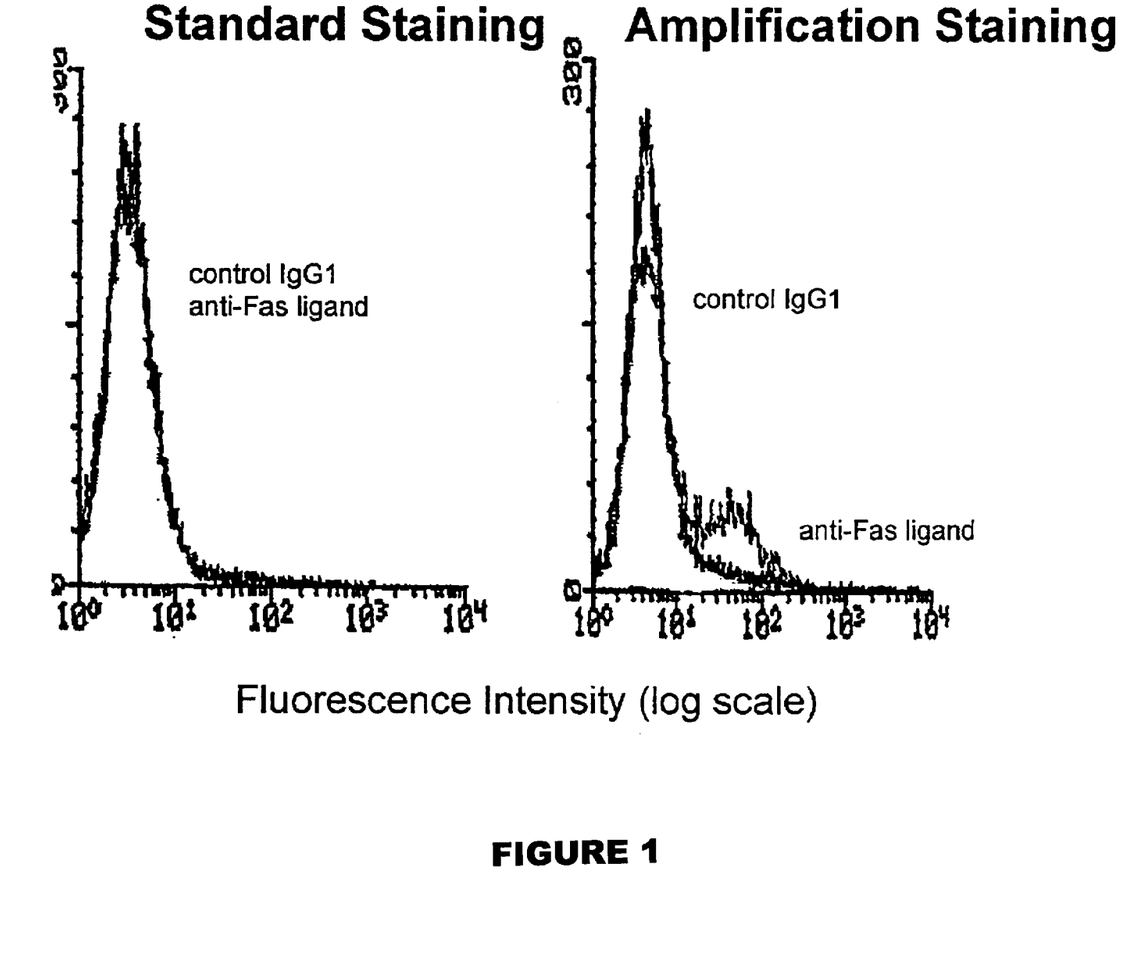
FIG. 1 shows fluorescence intensity for standard staining and amplification staining.
Figure 2:
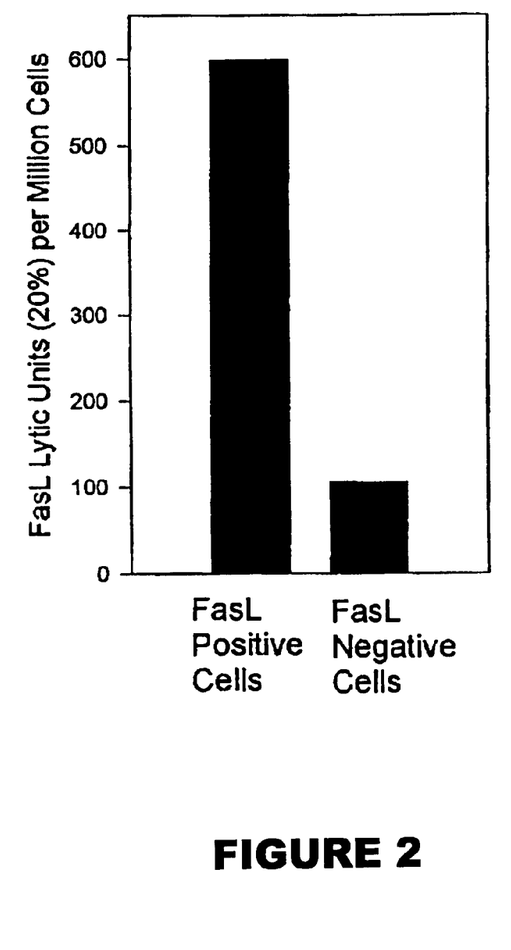
FIG. 2 shows FasL Lytic Units per million cells for FasL positive and negative cells.

We assessed peripheral blood mononuclear cells that had been stimulated with phytohemagglutinin and interleukin 2 for 2 days culture and then activated with phorbol myristic acetate and ionomycin for 1 day. Amplification staining of these cells showed that 10–15% of the cells were expressing enough Fas ligand to define a separate positive subpopulation (FIG. 1). To ascertain that this staining was significant in terms of the function of the cells, we sorted the positive population and the negative population by Fas and assessed their cytotoxic potential against Fas expressing Jurkat targets (FIG. 2). The results demonstrate that our amplification staining technique successful identified functionally significant levels of Fas ligand on the cell surface. Moreover, it shows that cells treated for amplification staining retained their viability and function, and further studies have demonstrated that the cells can continue to proliferate as well.

DETAILED DESCRIPTION OF THE PREFERRED EMBODIMENTS

The method of tyramide coating cells or particles for physical separation represents a new method for detecting and/or quantitating cellular analytes. The present invention offers a method which allows for better detection of cell surface molecules and moreover allows for the isolation of cells or particles expressing analytes by physical separation by using lower concentrations of antibodies, antibodies of lower affinity and will allow the isolation of cells and particles based on the expression of molecules previously incapable of being detected by less sensitive labeling methods. Hence, the present invention offers a more sensitive method for physical separation of cellular analytes in samples of cells or particles.

Standard Physical Separation

Physical separation of cells or particles may be achieved using a variety of methods, including magnetic separation, cellular panning, column separation, and FACS. The use of magnetic separation is described in Stanciu et al., *Journal of Immunological Methods*, 189:107–115, 1996; Luxembourg et al., *Nature Biotechnology*, 16:281–285, 1998; Sun et al., *Journal of Immunological Methods*, 205:73–79, 1997; Partington et al., *Journal of Immunological Methods*, 223:195–205, 1999; Nielson et al., *Journal of Immunological Methods*, 200:107–112, 1997; and Assenmacher et al., *The Journal of Immunology*, 161:2825–2832, 1998. The use of cellular panning is described Wysocki and Sato, *P.N.A.S.*, 75(6):2844–2848, 1978. Use of column separation is described in Davis et al., *Journal of Immunological Methods*, 175:247–257, 1994. FACS's described in Melamed, Lindman, and Mendelsohn *Flow Cytometry and Sorting* Wiley-Liss, New York, 1990.

Amplification Labeling

Amplification staining has been found to be of importance in the detection of cellular analytes for various immunological and immunogenetic procedures. For methods of immunohistochemistry (analysis of slide fixed tissues or cell samples by fluorescent microscopy) the use of enzyme based amplification staining methods has led to enhanced sensitivity.

The Catalyzed Reporter Deposition (CARD) method described by Bobrow et al. "Catalyzed Reporter Deposition, A Novel Method Of Signal Amplification", *Journal of Immunological Methods*, 125: 279–285 (1989) and 137: 103–112 (1991) is an amplification staining method used for both immunohistochemical methods, microplate immunoassays (such as ELISAs) as well as membrane immunoassays. Both the CARD method or the analyte dependent enzyme activation system refer to an enzyme system where an enzyme is coupled to a member of a specific binding pair, the enzyme then catalyzes the formation of an activated conjugate which is deposited wherever a receptor for the activated conjugate is immobilized. This system has led to methods for maximizing the sensitivity of methods aimed at the cellular localization of proteins and nucleic acids, especially in cases where target levels are known or suspected to be low. These methods have evolved to improve the sensitivity of both immunohistochemistry and in situ hybridization techniques.

Amplification labeling for physical separation of cells or particles is desirable and will allow isolation based on expression of analytes that are not expressed at levels that will permit isolation based on current technology, and it will allow the use of smaller amounts of binding partners (antibodies) to achieve physical separation.

Tyramide Coating Cells or Particles

For Physical Separation

Tyramide coating of live cells for flow cytometry is described in Kaplan, "METHODS FOR DETECTING AN ANALYTE OF INTEREST USING TYRAMIDE COATING TECHNOLOGY", U.S. patent application Ser. No. 09/229,001, filed Jan. 12, 1999, which is incorporated herein by reference in its entirety, including any drawings.

In order to enhance the sensitivity of physical separation of cells or particles, we have provided a system of amplified reporter deposition. The current method preferably employs the use of biotinylated antibodies specific for cell surface molecules, a steptavidin-horseradish peroxidase and the substrate peroxide and a reporter molecule such as tyramide. The enzyme reacts with its' substrate to produce oxygen radicals which interact with the phenolic group of tyramide to create a short lived radical activated phenolic substrate.

It is believed that the radical activated phenolic substrate binds with electron rich moieties such as tyrosine and tryptophan present in the proteins found on most cell surfaces. It is for this reason that in a preferred embodiment tyramide may be replaced with a phenolic molecule which can be attached to a binding partner. Tyramide can be readily attached to fluorescein, biotin or rhodamine as described in A.H.N. Hopman et al., "Rapid Synthesis of Biotin-, digoxigenin-, Trinitrophenyl-, and Fluorochrome-labeled Tyramides and Their Application for In Situ Hybridization using CARD Amplification", *The Journal of Histochemistry and Cytochemistry*, Vol. 46(6): 771–777, (1998), which is herein incorporated by reference in its entirety including any drawings. Binding of streptavidin adsorbed to plastic plates for panning solid phase particles for column-based separation, or streptavidin conjugated iron oxide particles for magnetic separation is used to accomplish the isolation of the targeted cells or particles. Alternatively, tyramide is directly conjugated to plastic plates, solid phase particles, or magnetic particles for physical separation.

We have investigated the potential of enzymatic amplification to enhance signals in labeling surface molecules for physical separation of cells or particles. KFL9 and K562 cells labeled with Anti-Fas ligand monoclonal antibody when incubated with enzymatic incubation steps will produce an increase in signal when compared to cells incubated without the enzymatic amplification step. The enhancement in the signal indicates that the use of this technology will allow more sensitivity in the detection of cell surface molecules which will be advantageous for both diagnostic and research applications.

A phenomenon of an aspect of amplification labeling of surface molecules has been termed "bystander labeling". Bystander labeling refers to the labeling of negative cells in test tubes that include both analyte positive and negative cells. When analyte negative cells are amplification stained for physical separation using control antibodies which should not bind the cell there is no detectable labeling of the cells other than background labeling which is commensurate with that found in standard labeling procedures. However, if there are both negative and positive analyte cells in the same test tube, the amplification labeling procedure may label both the positive and negative cells. The elimination of bystander labeling occurs in the amplification step of the method. By resuspending the cells in a low volume 25 to 100 microliters of FICOLL®HYPAQUE® (an aqueous solution comprising a neutral, branched hydrophilic sucrose polymer having an average molecular weight of 400,000 and sodium diatrizoate), pH 8.5 with or without the addition of exogenous protein such as milk protein the bystander labeling effect is reduced and almost eliminated. This step strengthens the overall specificity of the method, however it is still possible to differentiate analyte positive cells from analyte negative cells based on their respective signal without eliminating bystander labeling.

Cell surface analytes can be present on cell surfaces in amounts which are not easily detectable by current methods. For example, some cells have stimulated Fas ligand activity which can be measured in a cytotoxicity assay and is indicative of the presence of Fas ligand. However, labeling of some of these cells by standard labeling procedures is inconclusive for the presence of the cell surface molecule using standard physical separation means. Surprisingly, Fas ligand can be detected by tyramide coating the cell surface using serial amplification. The detection of Fas ligand on some cells will be positive when analyzed by cytotoxic activity, but will be inconclusive for Fas ligand when analyzed by standard labeling methods. These cells when analyzed by physical separation using serial amplification methods as described herein will be positive for the presence of the cell surface molecule Fas ligand.

Furthermore, we have shown that additional cycles of serial amplification for tyramide coating results in improved detection of cell surface analytes.

Those in the art will appreciate that the method of the invention can be used for a variety of physical separation analysis methods for analyte detection in cell samples.

EXAMPLES

The following examples serve to illustrate the method for amplification labeling cells for physical separation of the invention. These examples are in no way intended to limit the scope of the invention.

Example 1

Tyramide Coating Cells for Physical Separation

1. A sample of cells expressing or presumed to be expressing a cell surface analyte of interest are added to a test tube.
2. To this sample, antibody (or antibody conjugate) specific for the analyte is added in a physiological buffer, such as phosphate buffered isotonic saline with 0.005% azide and 1% bovine serum albumin, at room temperature. The cells are washed once in with the same medium without antibody.
3. Add a substance with enzymatic activity (streptavidin-horseradish peroxidase) that will bind to antibody or antibody conjugate. Cells are incubated in a physiological buffer (as above) at room temperature. The cells are washed in phosphate buffered isotonic saline.
4. Tyramide-biotin molecules and peroxide are added to the cells in a solution of FICOLL®HYPAQUE® (an aqueous solution comprising a neutral, branched hydrophilic sucrose polymer having an average molecular weight of 400,000 and sodium diatrizoate), pH 8.5 in a small or low volume 25 to 100 microliters in the presence or absence of exogenous proteins (such as milk protein). Cells are incubated at room temperature in a physiological buffer that does not contain azide. The cells are washed with phosphate buffered saline and once with phosphate buffered saline with added sodium azide and bovine serum albumin.

5. Streptavidin-iron oxide molecules are added to the cells in phosphate buffered saline with added sodium azide and bovine serum albumin. The cells are washed and then physically separated by exposing the cells to a magnetic field and washing away unbound cells. By adhering streptavidin to the bottom of a plastic culture dish, physical separation of the targeted cells is accomplished by panning. By binding of the cells to beads, physical separation is accomplished by column separation.

A washing step may be included between each of steps 1, 2, and 3. Steps 2 and 3 may be combined with the use of an antibody conjugated to an enzyme as shown below.

Example 2
Labeling of CD45 with Conjugated Monoclonal Antibody for Physical Separation 1. A sample of Jurkat cells are added to two test tubes, a control tube and experimental tube.
2. To the control sample control antibody conjugated with horseradish peroxidase is added and to the experimental sample antibody specific for CD45 conjugated with horseradish peroxidase. Both samples are suspended in a physiological buffer, such as isotonic saline with 0.005% sodium azide, at room temperature.
3. After the cells are washed, tyramide-biotin molecules and hydrogen peroxide are added to the samples in a solution of FICOLL®HYPAQUE® (an aqueous solution comprising a neutral, branched hydrophilic sucrose polymer having an average molecular weight of 400,000 and sodium diatrizoate), pH 8.5 in a small or low volume (25 to 100 microliters) in the presence or absence of exogenous proteins (such as milk protein). Cells are incubated at room temperature in a physiological buffer that does not contain azide.
4. Streptavidin-iron oxide molecules are added to the cells in phosphate buffered saline with added sodium azide and bovine serum albumin. The cells are washed and then physically separated by exposing the cells to a magnetic field and washing away unbound cells. By adhering streptavidin to the bottom of a plastic culture dish, physical separation of the targeted cells is accomplished by panning. By binding of the cells to beads, physical separation is accomplished by column separation. Antibodies directly conjugated to horseradish peroxidase will work well in the amplification procedure.

Example 3
Elimination of Bystander Staining for Physical Separation of Cells or Particles 1. A sample of Jurkat (CD5 positive) and K562 (CD5 negative) cells of approximately equal numbers is added to a test tube.
2. To this sample, antibody (or antibody conjugate) specific for the analyte, CD5, is added in a physiological buffer, such as phosphate buffered isotonic saline with 0.005% azide and 1% bovine serum albumin, at room temperature. The cells are washed once in with the same medium without antibody.
3. Add a substance with enzymatic activity (streptavidin-horseradish peroxidase) that will bind to antibody or antibody conjugate. Cells are incubated in a physiological buffer (as above) at room temperature. The cells are washed in phosphate buffered isotonic saline.
4. Tyramide-biotin molecules and peroxide are added to the cells in a solution of FICOLL®HYPAQUE® (an aqueous solution comprising a neutral, branched hydrophilic sucrose polymer having an average molecular weight of 400,000 and sodium diatrizoate), pH 8.5 in a small or low volume 25 to 100 microliters in the presence or absence of exogenous proteins (such as milk protein). Cells are incubated at room temperature in a physiological buffer that does not contain azide. The cells are washed with phosphate buffered saline and once with phosphate buffered saline with added sodium azide and bovine serum albumin.
5. Streptavidin-iron oxide molecules are added to the cells in phosphate buffered saline with added sodium azide and bovine serum albumin. The cells are washed and then physically separated by exposing the cells to a magnetic field and washing away unbound cells. By adhering streptavidin to the bottom of a plastic culture dish, physical separation of the targeted cells is accomplished by panning. By binding of the cells to beads, physical separation is accomplished by column separation.

Samples will contain CD5 positive and CD5 negative populations of approximately equal numbers.

Example 4
Amplification Labeling of Cells for Physical Separation

1. Place half a million cells in 12×75 mm squared round bottom tubes.
2. Wash the cells once with phosphate buffered isotonic saline (pH 7.3) with 1% bovine serum albumin and 0.005% sodium azide (referred to as staining buffer).
3. Add to the cells biotinylated antibody (0.5–1 microgram) specific for analyte in 50 microliters of staining buffer and incubate for 10 minutes at room temperature in the dark.
4. Wash the cells one or two times with staining buffer.
5. Add to the cells streptavidin conjugated with horseradish peroxidase in 50 microliters of staining buffer and incubate for 10 minutes at room temperature in the dark.
6. Wash the cells one time with phosphate buffered isotonic saline, pH 7.3.
7. Wash the cells one time with phosphate buffered isotonic saline, pH 7.3 containing 0.01% hydrogen peroxide.
8. Add to the cells biotinylated tyramide (1–1.5 mg/ml) in 50 microliters of Histopaque (Sigma brand name of FICOLL®HYPAQUE® (an aqueous solution comprising a neutral, branched hydrophilic sucrose polymer having an average molecular weight of 400,000 and sodium diatrizoate), density 1.077) containing 0.01% hydrogen peroxide. Incubate the suspension for 10 minutes at room temperature in the dark.
9. Wash the cells one time with phosphate buffered isotonic saline, pH 7.3 and one time with staining buffer.

10. Streptavidin-iron oxide molecules are added to the cells in phosphate buffered saline with added sodium azide and bovine serum albumin. The cells are washed and then physically separated by exposing the cells to a magnetic field and washing away unbound cells. By adhering streptavidin to the bottom of a plastic culture dish, physical separation of the targeted cells is accomplished by panning. By binding of the cells to beads, physical separation is accomplished by column separation.

Example 5
Serial Amplification Labeling Method

1. Place half a million cells in 12×75 mm squared round bottom tubes.
2. Wash the cells once with phosphate buffered isotonic saline (pH 7.3) with 1% bovine serum albumin and 0.005% sodium azide (referred to as staining buffer).
3. Add to the cells biotinylated antibody (0.5–1 microgram) specific for Fas ligand analyte in 50 microliters of staining buffer and incubate for 10 minutes at room temperature in the dark.
4. Wash the cells one or two times with staining buffer.
5. Add to the cells streptavidin conjugated with horseradish peroxidase in 50 microliters of staining buffer and incubate for 10 minutes at room temperature in the dark.
6. Wash the cells one time with phosphate buffered isotonic saline, pH 7.3.
7. Wash the cells one time with phosphate buffered isotonic saline, pH 7.3 containing 0.01% hydrogen peroxide.
8. Add to the cells biotinylated tyramide (1–1.5 mg/ml) in 50 microliters of Histopaque (Sigma brand name of FICOLL®HYPAQUE® (an aqueous solution comprising a neutral, branched hydrophilic sucrose polymer having an average molecular weight of 400,000 and sodium diatrizoate), density 1.077) containing 0.01% hydrogen peroxide. Incubate the suspension for 10 minutes at room temperature in the dark.
9. Wash the cells one time with phosphate buffered isotonic saline, pH 7.3 and one time with staining buffer.
10. Repeat steps 5–9 at least once.
11. Streptavidin-iron oxide molecules are added to the cells in phosphate buffered saline with added sodium azide and bovine serum albumin. The cells are washed and then physically separated by exposing the cells to a magnetic field and washing away unbound cells. By adhering streptavidin to the bottom of a plastic culture dish, physical separation of the targeted cells is accomplished by panning. By binding of the cells to beads, physical separation is accomplished by column separation.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods, substituents (such as buffers, conjugates, enzymes and substrates), and target materials described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the present methods can incorporate a variety of different cell types, physiological buffers, enzyme-substrate systems, and different target materials. Thus, such additional embodiments are within the scope of the present invention and the following claims.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A method of isolating cells or particles from a sample, wherein the cells or particles have an analyte of interest on the surface of said cells or particles, comprising: exposing particles or unfixed cells to a binding partner specific for the analyte of interest and a labeling molecule comprising tyramide, such that the bound cells or particles are coated with tyramide, and isolating said tyramide coated cells or particles with a physical separation device.

2. The method of claim 1, wherein said binding partner has enzymatic activity, the cells or particles are further contacted with a substrate, and the reaction of the substrate with the binding partner causes the tyramide coating.

3. The method of claim 1, wherein said method comprises, contacting the cells or particles expressing said analyte of interest with a first binding partner specific for said analyte of interest, and a second binding partner with enzymatic activity.

4. The method of claim 1, further comprising, contacting the cells or particles expressing said analyte of interest with a first binding partner specific for said analyte of interest, a second binding partner with enzymatic activity, said second binding partner specific for said first binding partner, a substrate for said second binding partner with enzymatic activity, and a labeling molecule comprising tyramide, wherein said second binding partner reacts with said substrate to cause tyramide coating of the cells or particles; and isolating the cells or particles with said physical separation device.

5. The method of claim 4, wherein said second binding partner comprises at least one enzyme selected from the group consisting of hydrolysases, peroxidases, oxidases, esterases, glycosidases and phosphatases.

6. The method of any one of claim 3 or 4, wherein said second binding partner comprises horseradish peroxidase.

7. The method of claim 4, wherein said second binding partner is a streptavidin-enzyme conjugate.

8. The method of claim 7, wherein said streptavidin-enzyme conjugate is selected from the group consisting of streptavidin-peroxidase, streptavidin-hydrolase, streptavidin-oxidase, streptavidin-gycosidase and streptavidin-phosphatase.

9. The method of claim 8, wherein said streptavidin-enzyme conjugate is streptavidin-horseradish peroxidase.

10. The method of any one of claim 1 or 4, wherein said cells or particles expressing said analyte of interest are mammalian cells.

11. The method of claim 10, wherein said mammalian cells are human cells obtained from a patient.

12. The method of claim 10, wherein said mammalian cells are selected from the group consisting of basal cells, epithelial cells, erythrocytes, platelets, lymphocytes, T-cells, B-cells, natural killer cells, granulocytes, monocytes, mast cells, Jurkat cells, neurocytes, neuroblasts, cytomegalic cells, dendritic cells, macrophages, blastomeres, endothelial cells, HeLa cells, tumor cells, interstitial cells, Kupffer cells, Langerhans' cells, Langhans cells, littoral cells, muscle cells, adipose cells, CHO cells, KFL9 cells, and K562 cells.

13. The method of claim 10, wherein said analyte of interest is a cell surface molecule selected from the group consisting of Fas ligand, CD1 through CD166, MHC class I, MHC class II, tumor antigens, viral antigens, IgG receptors, IgE receptors, complement C3a receptors, complement C5a receptors, complement CR1 receptors, complement CR3 receptors, T Cell receptors, B-Cell receptors histocompatibility antigens, and differentiation antigens.

14. The method of claim 13, wherein said cell surface molecule is not a natural component of the cell.

15. The method of claim 1, wherein the method comprises contacting the cells or particles expressing said analyte of interest with a first binding partner specific for said analyte of interest, a second binding partner with enzymatic activity, said second binding partner specific for said first binding partner, a third binding partner specific for a second cell surface molecule, a fourth binding partner with enzymatic activity, said fourth binding partner specific for said third binding partner, a substrate for said enzymatic activity of the second and the fourth binding partners, and a labeling molecule comprising tyramide, wherein said second and fourth binding partners react with said substrate to cause tyramide coating of the cells or particles; and, isolating the cells or particles with said physical separation device.

16. The method of any one of claims 1, 4, 15 and 11, wherein said tyramide is directly or indirectly bound to a magnetic substance and said physical separation device is a magnetic separation device.

17. The method of any one of claims 1, 4, 15 and 11, wherein said tyramide is directly or indirectly bound to a solid phase and said physical separation device is a cellular panning device.

18. The method of any one of claims 1, 4, 15 and 11, wherein said tyramide is directly or indirectly bound to a solid phase and said physical separation device is a column separation device.

19. The method of any one of claims 1, 4, 15 and 11, wherein said tyramide is directly or indirectly bound to a fluorescent molecule and said physical separation device is a fluorescence activated cell sorting device.

20. The method of any of claims 1, 4, 12, 15, and 11, wherein said cells or particles are live cells.

* * * * *